(12) United States Patent  
Johnson et al.

(10) Patent No.: US 7,608,099 B2
(45) Date of Patent: Oct. 27, 2009

(54) MEDICAL APPLIANCE DELIVERY APPARATUS AND METHOD OF USE

(75) Inventors: Liann M Johnson, Golden Valley, MN (US); Paul S Sherburne, Plymouth, MN (US); Alicia F. Heck, St. Louis Park, MN (US); Ricci D. Smelser, Maple Lake, MN (US); Eric K Mangiardi, Charlotte, NC (US)

(73) Assignee: Merit Medical Systems Inc., South Jordan, UT (US)

( * ) Notice: Subject to any disclaimer, the term of this patent is extended or adjusted under 35 U.S.C. 154(b) by 0 days.

(21) Appl. No.: 11/357,366

(22) Filed: Feb. 17, 2006

(65) Prior Publication Data

US 2006/0200222 A1    Sep. 7, 2006

Related U.S. Application Data

(63) Continuation of application No. 10/281,429, filed on Oct. 26, 2002, now abandoned.

(51) Int. Cl.
*A61F 2/06* (2006.01)
*A61B 17/00* (2006.01)

(52) U.S. Cl. .................. 623/1.11; 606/198; 606/108
(58) Field of Classification Search ............. 623/1.11; 606/198, 191, 194, 195
See application file for complete search history.

(56) References Cited

U.S. PATENT DOCUMENTS 3,196,876 A    7/1965    Roberts et al.

(Continued)

FOREIGN PATENT DOCUMENTS

EP    0 364 420 A1    4/1990

(Continued)

OTHER PUBLICATIONS

PCT Notification of Transmittal of the International Search Report, PCT International Search Report mailed Jun. 24, 2004 for PCT/US03/33967 (Filed Oct. 25, 2003).

(Continued)

*Primary Examiner*—Vy Q. Bui
(74) *Attorney, Agent, or Firm*—Alston & Bird LLP

(57) ABSTRACT

The present invention, in an exemplary embodiment, provides a stent deployment apparatus comprising excellent safety and stent placement and deployment features. An exemplary stent deployment apparatus in accordance with the present invention can facilitate the precise delivery of stents in a safe and repeatable fashion. In particular, a preferred deployment apparatus allows the physician to concentrate on correct placement without having to estimate extent of deployment by providing a physical safety mechanism that limits deployment to the critical deployment point. Moreover, to exceed this threshold, an audible and/or tactile indicator informs the physician that she can no longer retract the stent beyond this point. The stent deployment apparatus guidewire may also be extended rather than retracting the outer catheter to deliver the stent. Moreover, the distal tip is designed to comfortably guide the deployment apparatus through a diseased or occluded lumen so that the stent can be delivered in the most beneficial location. Additionally, the distal tip facilitates the removal of the deployment apparatus even if a defective stent is only partially radially expanded. In alternative embodiments, the stent deployment apparatus allows for the insertion of an optical scope to facilitate stent delivery.

28 Claims, 4 Drawing Sheets

U.S. PATENT DOCUMENTS

| | | | |
|---|---|---|---|
| 4,343,048 A | 8/1982 | Ross et al. | |
| 4,606,330 A | 8/1986 | Bonnet | |
| 4,665,906 A | 5/1987 | Jervis | |
| 4,680,031 A | 7/1987 | Alonso | |
| 4,733,665 A | 3/1988 | Palmaz | |
| 4,739,762 A | 4/1988 | Palmaz | |
| 4,820,262 A | 4/1989 | Finney | |
| 4,893,623 A | 1/1990 | Rosenbluth | |
| 5,019,085 A | 5/1991 | Hillstead | |
| 5,032,128 A | 7/1991 | Alonso | |
| 5,067,957 A | 11/1991 | Jervis | |
| 5,073,694 A | 12/1991 | Tessier et al. | |
| 5,102,417 A | 4/1992 | Palmaz | |
| 5,104,404 A | 4/1992 | Wolff | |
| 5,159,920 A * | 11/1992 | Condon et al. | 600/129 |
| 5,190,546 A | 3/1993 | Jervis | |
| 5,195,984 A | 3/1993 | Schatz | |
| 5,249,585 A | 10/1993 | Turner et al. | |
| 5,292,331 A | 3/1994 | Boneau | |
| 5,320,617 A | 6/1994 | Leach | |
| 5,345,057 A | 9/1994 | Muller | |
| 5,354,309 A | 10/1994 | Schnepp-Pesch et al. | |
| 5,356,423 A | 10/1994 | Tihon et al. | |
| 5,383,892 A | 1/1995 | Cardon et al. | |
| 5,409,453 A | 4/1995 | Lundquist et al. | |
| 5,421,955 A | 6/1995 | Lau et al. | |
| 5,433,723 A * | 7/1995 | Lindenberg et al. | 606/198 |
| 5,443,498 A | 8/1995 | Fontaine | |
| 5,449,373 A | 9/1995 | Pinchasik et al. | |
| 5,514,093 A | 5/1996 | Ellis et al. | |
| 5,514,154 A | 5/1996 | Lau et al. | |
| 5,534,287 A | 7/1996 | Lukic | |
| 5,549,644 A | 8/1996 | Lundquist et al. | |
| 5,588,949 A | 12/1996 | Taylor et al. | |
| 5,591,157 A | 1/1997 | Hennings et al. | |
| 5,591,197 A | 1/1997 | Orth et al. | |
| 5,593,442 A | 1/1997 | Klein | |
| 5,597,378 A | 1/1997 | Jervis | |
| 5,601,591 A | 2/1997 | Edwards et al. | |
| 5,601,593 A | 2/1997 | Freitag | |
| 5,603,698 A | 2/1997 | Roberts et al. | |
| 5,609,629 A | 3/1997 | Fearnot et al. | |
| 5,618,300 A | 4/1997 | Marin | |
| 5,628,788 A | 5/1997 | Pinchuk | |
| 5,643,312 A | 7/1997 | Fischell et al. | |
| 5,662,713 A | 9/1997 | Andersen et al. | |
| 5,667,522 A | 9/1997 | Flomenbilt et al. | |
| 5,681,346 A | 10/1997 | Orth et al. | |
| 5,690,644 A | 11/1997 | Yurek et al. | |
| 5,695,499 A | 12/1997 | Helgrson et al. | |
| 5,702,418 A | 12/1997 | Ravenscroft | |
| 5,707,386 A | 1/1998 | Schnepp-Pesch et al. | |
| 5,713,949 A | 2/1998 | Jayaraman | |
| 5,716,393 A | 2/1998 | Lindenberg et al. | |
| 5,733,303 A | 3/1998 | Israel et al. | |
| 5,741,333 A | 4/1998 | Frid | |
| 5,746,692 A | 5/1998 | Bacich et al. | |
| 5,755,776 A | 5/1998 | Al-Saadon | |
| 5,759,192 A | 6/1998 | Saunders | |
| 5,766,238 A | 6/1998 | Lau et al. | |
| 5,776,140 A | 7/1998 | Cottone | |
| 5,776,161 A | 7/1998 | Globerman | |
| 5,780,807 A | 7/1998 | Saunders | |
| 5,782,838 A | 7/1998 | Beyar et al. | |
| 5,803,080 A | 9/1998 | Freitag | |
| 5,807,404 A | 9/1998 | Richter | |
| 5,814,063 A | 9/1998 | Freitag | |
| 5,817,102 A | 10/1998 | Johnson et al. | |
| 5,824,042 A | 10/1998 | Lombardi et al. | |
| 5,824,058 A | 10/1998 | Ravenscroft et al. | |
| 5,830,179 A | 11/1998 | Mikus et al. | |
| 5,833,694 A | 11/1998 | Poncet | |
| 5,836,966 A | 11/1998 | St. Germain | |
| 5,837,313 A | 11/1998 | Ding et al. | |
| 5,843,120 A | 12/1998 | Israel et al. | |
| 5,860,999 A | 1/1999 | Schnepp-Pesch et al. | |
| 5,873,904 A | 2/1999 | Ragheb et al. | |
| 5,876,445 A | 3/1999 | Anderson et al. | |
| 5,876,448 A | 3/1999 | Thompson et al. | |
| 5,876,449 A | 3/1999 | Starck et al. | |
| 5,879,370 A | 3/1999 | Fischell et al. | |
| 5,902,333 A | 5/1999 | Roberts et al. | |
| 5,902,475 A | 5/1999 | Trozera et al. | |
| 5,911,732 A | 6/1999 | Hojeibane | |
| 5,922,020 A | 7/1999 | Klein et al. | |
| 5,922,393 A | 7/1999 | Jayaraman | |
| 5,935,162 A | 8/1999 | Dang | |
| 5,954,729 A | 9/1999 | Bachmann et al. | |
| 5,968,052 A * | 10/1999 | Sullivan et al. | 623/1.11 |
| 5,968,070 A | 10/1999 | Bley et al. | |
| 5,968,091 A | 10/1999 | Pinchuk et al. | |
| 5,972,018 A | 10/1999 | Israel et al. | |
| 5,980,552 A | 11/1999 | Pinchasik et al. | |
| 5,984,964 A | 11/1999 | Roberts et al. | |
| 6,017,365 A | 1/2000 | Von Oepen | |
| 6,019,778 A | 2/2000 | Wilson et al. | |
| 6,022,371 A | 2/2000 | Killion | |
| 6,033,435 A | 3/2000 | Penn et al. | |
| 6,042,597 A | 3/2000 | Kveen et al. | |
| 6,048,361 A | 4/2000 | Von Oepen | |
| 6,051,021 A | 4/2000 | Frid | |
| 6,053,941 A | 4/2000 | Lindenberg et al. | |
| 6,056,775 A | 5/2000 | Borghi et al. | |
| 6,059,811 A | 5/2000 | Pinchasik et al. | |
| 6,086,528 A | 7/2000 | Adair | |
| 6,096,070 A | 8/2000 | Ragheb et al. | |
| 6,099,560 A | 8/2000 | Penn et al. | |
| 6,131,266 A | 10/2000 | Saunders | |
| 6,132,461 A | 10/2000 | Thompson | |
| 6,136,006 A | 10/2000 | Johnson et al. | |
| 6,146,403 A | 11/2000 | St. Germain | |
| 6,146,416 A | 11/2000 | Andersen et al. | |
| 6,156,035 A | 12/2000 | Songer | |
| 6,156,052 A | 12/2000 | Richter et al. | |
| 6,162,231 A | 12/2000 | Mikus et al. | |
| 6,174,329 B1 | 1/2001 | Callol et al. | |
| 6,179,867 B1 | 1/2001 | Cox | |
| 6,203,550 B1 * | 3/2001 | Olson | 606/108 |
| 6,203,568 B1 | 3/2001 | Lombardi et al. | |
| 6,217,608 B1 | 4/2001 | Penn et al. | |
| 6,238,430 B1 | 5/2001 | Klumb et al. | |
| 6,270,524 B1 | 8/2001 | Kim | |
| 6,299,622 B1 | 10/2001 | Snow et al. | |
| 6,302,906 B1 | 10/2001 | Goicoechea et al. | |
| 6,306,141 B1 | 10/2001 | Jervis | |
| 6,315,794 B1 | 11/2001 | Richter | |
| 6,322,586 B1 | 11/2001 | Monroe et al. | |
| 6,325,790 B1 | 12/2001 | Trotta | |
| 6,355,063 B1 | 3/2002 | Calcote | |
| 6,361,557 B1 | 3/2002 | Gittings et al. | |
| 6,369,355 B1 | 4/2002 | Saunders | |
| 6,375,676 B1 | 4/2002 | Cox | |
| 6,380,457 B1 | 4/2002 | Yurek et al. | |
| 6,423,084 B1 | 7/2002 | St. Germain | |
| 6,428,538 B1 * | 8/2002 | Blewett et al. | 606/46 |
| 6,428,570 B1 | 8/2002 | Globerman | |
| 6,440,162 B1 | 8/2002 | Cox et al. | |
| 6,443,982 B1 | 9/2002 | Israel et al. | |
| 6,451,025 B1 | 9/2002 | Jervis | |
| 6,454,789 B1 | 9/2002 | Chen et al. | |
| 6,461,381 B2 | 10/2002 | Israel et al. | |
| 6,464,720 B2 | 10/2002 | Boatman et al. | |
| 6,464,722 B2 | 10/2002 | Israel et al. | |
| 6,475,234 B1 | 11/2002 | Richter et al. | |

| | | |
|---|---|---|
| 6,488,697 B1 | 12/2002 | Ariura et al. |
| 6,508,834 B1 | 1/2003 | Pinchasik et al. |
| 6,514,245 B1 | 2/2003 | Williams et al. |
| 6,514,285 B1 | 2/2003 | Pinchasik |
| 6,517,569 B2 | 2/2003 | Mikus et al. |
| 6,533,805 B1 | 3/2003 | Jervis |
| 6,540,777 B2 | 4/2003 | Stenzel |
| 6,569,085 B2 | 5/2003 | Kortenbach et al. |
| 6,569,194 B1 | 5/2003 | Pelton |
| 6,572,646 B1 | 6/2003 | Boylan et al. |
| 6,589,276 B2 | 7/2003 | Pinchasik et al. |
| 6,607,551 B1 | 8/2003 | Sullivan et al. |
| 6,613,078 B1 | 9/2003 | Barone |
| 6,620,193 B1 | 9/2003 | Lau et al. |
| 6,623,491 B2 | 9/2003 | Thompson |
| 6,626,902 B1 | 9/2003 | Kucharczyk et al. |
| 6,635,084 B2 | 10/2003 | Israel et al. |
| 6,638,293 B1 | 10/2003 | Makower et al. |
| 6,638,300 B1 | 10/2003 | Frantzen |
| 6,638,302 B1 | 10/2003 | Curcio et al. |
| 6,641,607 B1 | 11/2003 | Hossainy et al. |
| 6,641,608 B1 | 11/2003 | Pulnev |
| 6,641,609 B2 | 11/2003 | Globerman |
| 6,641,611 B2 | 11/2003 | Jayaraman |
| 6,645,239 B1 | 11/2003 | Park et al. |
| 6,645,240 B2 | 11/2003 | Yee |
| 6,645,242 B1 | 11/2003 | Quinn |
| 6,652,573 B2 | 11/2003 | von Oepen |
| 6,652,575 B2 | 11/2003 | Wang |
| 6,653,426 B2 | 11/2003 | Alvarado et al. |
| 6,656,201 B2 | 12/2003 | Ferrera et al. |
| 6,656,211 B1 | 12/2003 | DiCaprio |
| 6,656,214 B1 | 12/2003 | Fogarty et al. |
| 6,656,217 B1 | 12/2003 | Herzog, Jr. et al. |
| 6,656,351 B2 | 12/2003 | Boyle |
| 6,660,030 B2 | 12/2003 | Shaolian et al. |
| 6,660,034 B1 | 12/2003 | Mandrusov et al. |
| 6,660,827 B2 | 12/2003 | Loomis et al. |
| 6,663,660 B2 | 12/2003 | Dusbabek et al. |
| 6,663,664 B1 | 12/2003 | Pacetti |
| 6,663,880 B1 | 12/2003 | Roorda et al. |
| 6,664,335 B2 | 12/2003 | Krishnan |
| 6,666,881 B1 | 12/2003 | Richter et al. |
| 6,666,884 B1 | 12/2003 | Webster |
| 6,669,716 B1 | 12/2003 | Gilson et al. |
| 6,669,718 B2 | 12/2003 | Besselink |
| 6,669,720 B1 | 12/2003 | Pierce |
| 6,669,721 B1 | 12/2003 | Bose et al. |
| 6,669,722 B2 | 12/2003 | Chen et al. |
| 6,669,723 B2 | 12/2003 | Killion et al. |
| 6,673,101 B1 | 1/2004 | Fitzgerald et al. |
| 6,673,102 B1 | 1/2004 | Vonesh et al. |
| 6,673,103 B1 | 1/2004 | Golds et al. |
| 6,673,104 B2 | 1/2004 | Barry |
| 6,673,105 B1 | 1/2004 | Chen |
| 6,673,107 B1 | 1/2004 | Brandt et al. |
| 6,673,154 B1 | 1/2004 | Pacetti et al. |
| 6,676,692 B2 | 1/2004 | Rabkin et al. |
| 6,676,693 B1 | 1/2004 | Belding et al. |
| 6,676,697 B1 | 1/2004 | Richter |
| 6,679,910 B1 | 1/2004 | Granada |
| 6,679,911 B2 | 1/2004 | Burgermeister |
| 6,685,736 B1 | 2/2004 | White et al. |
| 6,685,745 B2 | 2/2004 | Reever |
| 6,689,157 B2 | 2/2004 | Madrid et al. |
| 6,689,158 B1 | 2/2004 | White et al. |
| 6,692,483 B2 | 2/2004 | Vardi et al. |
| 6,692,522 B1 | 2/2004 | Richter |
| 6,695,809 B1 | 2/2004 | Lee |
| 6,695,812 B2 | 2/2004 | Estrada et al. |
| 6,695,833 B1 | 2/2004 | Frantzen |
| 6,695,862 B2 | 2/2004 | Cox et al. |
| 6,695,876 B1 | 2/2004 | Marotta et al. |
| 6,699,274 B2 | 3/2004 | Stinson |
| 6,699,276 B2 | 3/2004 | Sogard et al. |
| 6,699,277 B1 | 3/2004 | Freidberg et al. |
| 6,702,849 B1 | 3/2004 | Dutta et al. |
| 6,702,850 B1 | 3/2004 | Byun et al. |
| 6,706,061 B1 | 3/2004 | Fischell et al. |
| 6,706,062 B2 | 3/2004 | Vardi et al. |
| 6,709,440 B2 | 3/2004 | Callol et al. |
| 6,709,451 B1 | 3/2004 | Noble et al. |
| 6,712,846 B1 | 3/2004 | Kraus et al. |
| 6,716,240 B2 | 4/2004 | Fischell et al. |
| 6,719,782 B1 | 4/2004 | Chuter |
| 6,719,991 B2 | 4/2004 | Darouiche et al. |
| 6,723,071 B2 | 4/2004 | Gerdts et al. |
| 6,723,113 B1 | 4/2004 | Shkolnik |
| 6,723,120 B2 | 4/2004 | Yan |
| 6,723,121 B1 | 4/2004 | Zhong |
| 6,723,373 B1 | 4/2004 | Narayanan et al. |
| 6,726,712 B1 | 4/2004 | Raeder-Devens et al. |
| 6,730,064 B2 | 5/2004 | Ragheb et al. |
| 6,730,116 B1 | 5/2004 | Wolinsky et al. |
| 6,730,117 B1 | 5/2004 | Tseng et al. |
| 6,733,521 B2 | 5/2004 | Chobotov et al. |
| 6,733,523 B2 | 5/2004 | Shaolian et al. |
| 6,733,524 B2 | 5/2004 | Tseng et al. |
| 6,736,828 B1 | 5/2004 | Adams et al. |
| 6,736,838 B1 | 5/2004 | Richter |
| 6,740,113 B2 | 5/2004 | Vrba |
| 6,740,114 B2 | 5/2004 | Burgermeister |
| 6,740,115 B2 | 5/2004 | Lombardi et al. |
| 6,743,219 B1 | 6/2004 | Dwyer et al. |
| 6,746,423 B1 | 6/2004 | Wantink |
| 6,746,475 B1 | 6/2004 | Rivelli, Jr. |
| 6,746,476 B1 | 6/2004 | Hojeibane |
| 6,746,479 B2 | 6/2004 | Ehr et al. |
| 6,746,482 B2 | 6/2004 | Ung-Chhun |
| 6,749,627 B2 | 6/2004 | Thompson et al. |
| 6,749,629 B1 | 6/2004 | Hong et al. |
| 6,752,819 B1 | 6/2004 | Brady et al. |
| 6,752,825 B2 | 6/2004 | Eskuri |
| 6,752,826 B2 | 6/2004 | Holloway et al. |
| 6,752,829 B2 | 6/2004 | Kocur et al. |
| 6,753,071 B1 | 6/2004 | Pacetti |
| 6,755,855 B2 | 6/2004 | Yurek et al. |
| 6,756,007 B2 | 6/2004 | Pletzer et al. |
| 6,758,858 B2 | 7/2004 | McCrea et al. |
| 6,758,859 B1 | 7/2004 | Dang et al. |
| 6,761,703 B2 | 7/2004 | Miller et al. |
| 6,761,708 B1 | 7/2004 | Chiu et al. |
| 6,761,731 B2 | 7/2004 | Majercak |
| 6,761,733 B2 | 7/2004 | Chobotov et al. |
| 6,764,505 B1 | 7/2004 | Hossainy et al. |
| 6,764,506 B2 | 7/2004 | Roubin et al. |
| 6,764,507 B2 | 7/2004 | Shanley et al. |
| 6,764,519 B2 | 7/2004 | Whitmore, III |
| 6,770,086 B1 | 8/2004 | Girton |
| 6,770,088 B1 | 8/2004 | Jang |
| 6,770,091 B2 | 8/2004 | Richter et al. |
| 6,773,446 B1 | 8/2004 | Dwyer et al. |
| 6,773,447 B2 | 8/2004 | Laguna |
| 6,773,448 B2 | 8/2004 | Kusleika et al. |
| 6,774,157 B2 | 8/2004 | DelMain |
| 6,774,278 B1 | 8/2004 | Ragheb et al. |
| 6,776,792 B1 | 8/2004 | Yan et al. |
| 6,776,793 B2 | 8/2004 | Brown et al. |
| 6,776,795 B2 | 8/2004 | Pelton |
| 6,776,796 B2 | 8/2004 | Falotico et al. |
| 6,780,182 B2 | 8/2004 | Bowman et al. |
| 6,780,199 B2 | 8/2004 | Solar et al. |
| 6,786,918 B1 | 9/2004 | Krivoruchko et al. |
| 6,786,929 B2 | 9/2004 | Gambale et al. |
| 6,790,220 B2 | 9/2004 | Morris et al. |
| 6,790,222 B2 | 9/2004 | Kugler et al. |

| | | |
|---|---|---|
| 6,790,223 B2 | 9/2004 | Reever |
| 6,790,227 B2 | 9/2004 | Burgermeister |
| 6,790,228 B2 | 9/2004 | Hossainy et al. |
| 6,796,997 B1 | 9/2004 | Penn et al. |
| 6,797,217 B2 | 9/2004 | McCrea et al. |
| 6,800,081 B2 | 10/2004 | Parodi |
| 6,800,089 B1 | 10/2004 | Wang |
| 6,802,846 B2 | 10/2004 | Hauschild et al. |
| 6,802,849 B2 | 10/2004 | Blaeser et al. |
| 6,802,859 B1 | 10/2004 | Pazienza et al. |
| 6,805,702 B1 | 10/2004 | Chen et al. |
| 6,805,703 B2 | 10/2004 | McMorrow |
| 6,805,704 B1 | 10/2004 | Hoyns |
| 6,805,705 B2 | 10/2004 | Hong et al. |
| 6,805,706 B2 | 10/2004 | Solovay et al. |
| 6,805,707 B1 | 10/2004 | Hong et al. |
| 6,805,709 B1 | 10/2004 | Schaldach et al. |
| 6,805,898 B1 | 10/2004 | Wu et al. |
| 6,808,529 B2 | 10/2004 | Fulkerson |
| 6,808,533 B1 | 10/2004 | Goodwin et al. |
| 6,843,802 B1 | 1/2005 | Villalobos et al. |
| 6,860,898 B2 | 3/2005 | Stack et al. |
| 6,899,727 B2 | 5/2005 | Armstrong et al. |
| 6,911,039 B2 | 6/2005 | Shiu et al. |
| 6,942,674 B2 | 9/2005 | Belef et al. |
| 6,953,475 B2 | 10/2005 | Shaolian et al. |
| 6,972,054 B2 | 12/2005 | Kerrigan |
| 6,984,244 B2 | 1/2006 | Perez et al. |
| 6,989,024 B2 | 1/2006 | Herbert et al. |
| 7,011,675 B2 | 3/2006 | Hemerick et al. |
| 2001/0016767 A1 | 8/2001 | Wilson et al. |
| 2001/0016768 A1 | 8/2001 | Wilson et al. |
| 2001/0027339 A1 | 10/2001 | Boatman et al. |
| 2001/0037138 A1 | 11/2001 | Wilston et al. |
| 2002/0002396 A1 | 1/2002 | Fulkerson |
| 2002/0042650 A1 | 4/2002 | Vardi et al. |
| 2002/0111672 A1 | 8/2002 | Kim et al. |
| 2002/0156524 A1 | 10/2002 | Ehr et al. |
| 2002/0161425 A1 | 10/2002 | Hemerick et al. |
| 2002/0183763 A1 | 12/2002 | Callot et al. |
| 2002/0183831 A1 | 12/2002 | Rolando et al. |
| 2002/0183832 A1 | 12/2002 | Penn et al. |
| 2002/0193866 A1 | 12/2002 | Saunders |
| 2002/0198593 A1 | 12/2002 | Gomez et al. |
| 2003/0004567 A1 | 1/2003 | Boyle et al. |
| 2003/0028240 A1 | 2/2003 | Nolting et al. |
| 2003/0036793 A1 | 2/2003 | Richter et al. |
| 2003/0045925 A1 | 3/2003 | Jayaraman |
| 2003/0050690 A1 | 3/2003 | Kveen et al. |
| 2003/0074045 A1 | 4/2003 | Buzzard et al. |
| 2003/0077310 A1 | 4/2003 | Pathak et al. |
| 2003/0083734 A1 | 5/2003 | Friedrich et al. |
| 2003/0105511 A1 | 6/2003 | Welsh et al. |
| 2003/0105513 A1 | 6/2003 | Moriuchi et al. |
| 2003/0114919 A1 | 6/2003 | McQuiston et al. |
| 2003/0125799 A1 | 7/2003 | Limon |
| 2003/0139796 A1 | 7/2003 | Sequin et al. |
| 2003/0139803 A1 | 7/2003 | Sequin et al. |
| 2003/0144671 A1 | 7/2003 | Brooks et al. |
| 2003/0144726 A1 | 7/2003 | Majercak et al. |
| 2003/0144731 A1 | 7/2003 | Wolinsky et al. |
| 2003/0149469 A1 | 8/2003 | Wolinsky et al. |
| 2003/0158596 A1 | 8/2003 | Ikeuchi et al. |
| 2004/0006380 A1 | 1/2004 | Buck et al. |
| 2004/0093056 A1 | 5/2004 | Johnson et al. |

FOREIGN PATENT DOCUMENTS

| | | |
|---|---|---|
| EP | 0 516 189 A1 | 12/1992 |
| JP | 2001-299932 | 10/2001 |
| WO | WO 92/11824 | 7/1992 |
| WO | WO 97/10011 | 3/1997 |
| WO | WO 97/14456 | 4/1997 |
| WO | WO 97/40739 | 11/1997 |
| WO | WO 98/20811 | 5/1998 |
| WO | WO 99/49812 | 10/1999 |
| WO | WO 99/62430 | 12/1999 |
| WO | WO 00/09041 | 2/2000 |
| WO | WO 00/45742 | 8/2000 |
| WO | WO 01/76508 A2 | 10/2001 |
| WO | WO 02/19948 A2 | 3/2002 |
| WO | WO 02/083038 A2 | 10/2002 |

OTHER PUBLICATIONS

Related U.S. Appl. No. 10/404,197, filed Mar. 31, 2003, entitled "Medical Appliance Optical Delivery and Deployment Apparatus and Method."

Office Action from corresponding Japanese Patent Application No. 2004-548493, completed Jul. 18, 2008.

Office Action from related U.S. Appl. No. 10/404,197, mailed Jul. 24, 2006.

Final Office Action from related U.S. Appl. No. 10/404,197, mailed May 4, 2007.

Office Action from related U.S. Appl. No. 10/404,197, mailed Nov. 9, 2007.

Final Office Action from related U.S. Appl. No. 10/404,197, mailed May 5, 2008.

Office Action from corresponding Japanese Patent Application No. 2004-548493, completed May 12, 2009.

* cited by examiner

MEDICAL APPLIANCE DELIVERY APPARATUS AND METHOD OF USE

CROSS-REFERENCE TO RELATED APPLICATIONS

This application is a continuation of U.S. application Ser. No. 10/281,429, filed Oct. 26, 2002, now abandoned which is hereby incorporated herein in its entirety by reference.

FIELD OF THE INVENTION

The present invention relates generally to medical devices directed to the prevention of nonvascular vessel or passageway occlusion, and more particularly to stent deployment apparatuses and methods for utilizing these devices in the treatment of both benign and malignant conditions.

BACKGROUND OF THE INVENTION

Stents are devices that are inserted into a vessel or passage to keep the lumen open and prevent closure due to a stricture, external compression, or internal obstruction. In particular, stents are commonly used to keep blood vessels open in the coronary arteries and they are frequently inserted into the ureters to maintain drainage from the kidneys, the bile duct for pancreatic cancer or cholangiocarcinoma or the esophagus for strictures or cancer. Nonvascular stenting involves a range of anatomical lumens and various therapeutic approaches, however, accuracy of installation is universally important.

In order to serve its desired function, the stent must be delivered precisely and oriented correctly. In order to facilitate the delivery of stents, medical device companies began to design deployment apparatuses that allow physicians to deploy stents more precisely. Unfortunately, guidance of the stent has substantially remained a function of physician skill resulting from substantial practice. This fact has become particularly evident with the advent of radially expanding stents. If after full deployment of the stent, the physician discovers the stent has been implanted incorrectly, there is no conventional way of correcting the error short of removing the stent. In particular, as a rule of thumb, once the exterior catheter, of conventional delivery devices, has been retracted beyond 60%, it generally cannot be realigned with respect to the stent. As a result, physicians must be sure of their stent placement prior to deploying the stent beyond the 60% point. We will refer to this 60% point throughout the application as the critical deployment point.

Conventional stent delivery devices, however, do not have any safety mechanism to prevent excessive deployment of a misaligned stent. In fact, conventional delivery devices require the physician to estimate extent of deployment, which results in either overly conservative or excessive deployment—both of which leads to stent misplacement.

An additional limitation of conventional stent delivery devices is the distal tip of conventional stent delivery devices are not adequately designed to (1) facilitate the clearance of obstructed lumen, or (2) facilitate the removal of the delivery device once the stent is radially expanded. In particular, most distal tips are not configured to comfortably guide the delivery device through a diseased or occluded lumen so that the stent can be delivered in the most beneficial location. Moreover, once the stent is radially expanded conventional designs rely exclusively on dimensional mismatching to ensure proper removal of the delivery device. In the event the stent does not adequately expand to preset dimensions, a conventional delivery device would be stuck in the patient until some invasive procedure is performed to remove it and the defective stent.

Therefore, there remains an existing need for a stent deployment apparatuses that has a safety mechanism to prevent excessive deployment of a misaligned stent. Preferably it would be desirable if the safety mechanism had a physical and/or audible indication means to inform the physician when she has reached maximum reversible deployment. As an additional safety feature, there is an existing need for a distal tip designed to allow for the removal of the deployment apparatus even if the stent does not radially expand to its preset expansion diameter. An existing need also exists for a stent deployment apparatus that has a distal tip adequately configured to navigate through diseased and/or occluded lumens so that the stent can be delivered to this target area.

There also remains an existing need for a stent deployment apparatus that increases physician control during stent deployment. Moreover, there exists a need for a stent deployment apparatus that allows for the insertion of an optical scope to facilitate stent delivery.

SUMMARY OF EXEMPLARY EMBODIMENTS

It is a principal objective of an exemplary stent deployment apparatus in accordance with the present invention to provide a device that can facilitate the precise delivery of stents in a safe and repeatable fashion. In the furtherance of this and other objectives, a preferred deployment apparatus allows the physician to concentrate on correct placement without having to estimate extent of deployment. In particular, in a preferred embodiment, the present deployment apparatus has a physical safety mechanism that limits deployment to the critical deployment point (i.e., ~60%). The critical deployment point may range form 5% to 95% but is preferably about 60%. At this point, if the physician is satisfied with placement, she can engage the safety means to what we refer to as the Proceed Orientation (PO) and fully deploy the stent. It is preferred that when the safety mechanism is engaged to the PO, a physical twist and a possible audible indicator sounds to inform the physician that if she deploys the stent any further, she can no longer retract the stent beyond this point. Though the present stent and delivery system eliminates the need for repositioning, such safety features are still preferable. In a preferred embodiment, the slight audible indication is the sound of a tab or stop snapping to allow free deployment of the stent.

An additional objective of a preferred embodiment of the present invention is to provide a stent deployment apparatus where the handle portion is held and the outer tubular member of the device is retracted.

Yet another objective in accordance with the present invention is to provide a deployment apparatus having a distal tip designed to facilitate the clearance of obstructed lumen. In the furtherance of this and other objectives, the exemplary distal tips are configured to comfortably guide the deployment apparatus through a diseased or occluded lumen so that the stent can be delivered in the most beneficial location.

Still another objective of a preferred deployment apparatus in accordance with the present invention is to provide a distal tip that facilitates the removal of the deployment apparatus once the stent is radially expanded. In the furtherance of this and other objectives, the distal tip is designed to clear the stent during removal, in the event the stent does not adequately expand to preset dimensions. In a preferred embodiment, removal is facilitated by providing a distal tip that has a substantially bidirectional conic shape. This allows for the removal of the present deployment apparatus, while conventional deployment apparatuses would be stuck in the patient until some invasive procedure was performed to remove it and the defective stent. This results from the fact that conventional deployment apparatus designs rely exclusively on dimensional mismatching between the distal tip and the radially expanded stent to ensure proper removal of the deployment apparatus. As a function of the design of the present invention, the compressed stent is adequately retained in place and does not prematurely creep up the proximally facing conic end of the distal tip and prematurely deploy.

An additional objective in accordance with an exemplary embodiment of the present invention is to provide a stent deployment apparatus that allows for the insertion of an optical scope to facilitate stent delivery. In the furtherance of this and other objectives, the device is capable of letting a flexible optical scope of about 5-6 mm diameter be coupled along the exterior of the outer tubular member thereof. Alternatively, it is envisioned that an ultra thin optical scope may pass along side the guidewire through the internal diameter of the internal tubular member of the device.

In addition to the above objectives, an exemplary stent deployment apparatus preferably has one or more of the following characteristics: (1) applicable for various interventional applications such as addressing stenosis; (2) biocompatible; (3) compliant with radially expanding stents; (4) capable of distal or proximal stent release; (5) smooth and clean outer surface; (6) length of the device variable according to the insertion procedure to be employed; (7) outer dimension as small as possible (depends on the diameter of crimped stent); (8) dimensions of the device must offer enough space for the crimped stent; (9) radiopaque markers, preferably on the inner tubular member, to indicate proximal and distal ends of the stent; (10) sufficient flexibility to adapt to luminal curvatures without loss of ability to push or pull; (11) low friction between the inner tubular member and outer tubular member; (12) sufficient resistance to kinking; (13) good deployment, ability to reposition partially deployed stent; (14) added with a scale to observe the stent position during the insertion procedure; (15) insertion procedure should require low force; or (16) sufficiently economical to manufacture so as to make the deployment apparatus disposable.

Further objectives, features and advantages of the invention will be apparent from the following detailed description taken in conjunction with the accompanying drawings.

DETAILED DESCRIPTION OF AN EMBODIMENT

Figure 1:
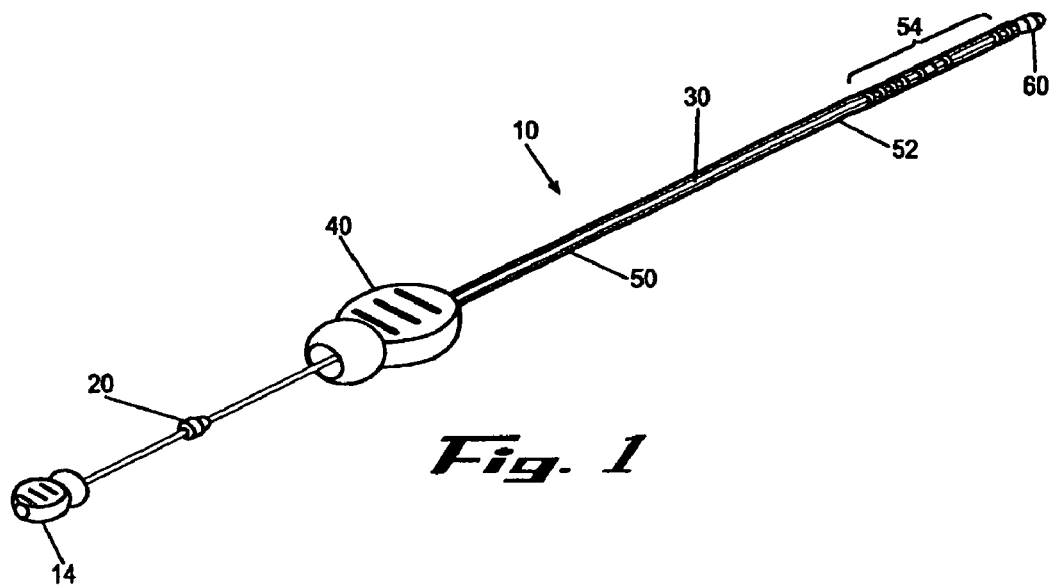
FIG. 1 is a perspective view of a device for delivering and deploying a radially self-expanding stent in accordance with the present invention.

A general problem in the diagnosis and therapy of both vascular and nonvascular anomalies is the fact that the instruments must be inserted into or pass the area of maximum diameter of about 15 mm. As a result, the inserted instruments take away a very large portion of the free lumen and may increase the danger of injury to the patient.

Therefore, it is the primary objective of the present invention to provide an instrument, which con be inserted gently, ensures a good utilization of the available space and makes it possible to carry out active therapeutic measures, wherein the instrument is to be particularly suitable for the introduction and placement of stents.

A preferred embodiment of the present deployment apparatus comprises inner and outer tubular members interactively coupled with each other in a manner that one can move rotationally and proximally or distally with respect to the other. The tubular members are preferably nonpyrogenic. In order to deliver the stent, the deployment apparatus comprises a distal tip and a stent retaining hub, between which the stent is placed. The distal tip and the stent-retaining hub are both functionally coupled with the inner tubular member. The inner tubular member terminates with a luer or in a preferred embodiment, a proximal handle similar to the outer handle hub. The luer is preferably a female threaded luer, but alternative termini are within the skill of the stent deployment device engineer. In fact, a suitable alternative would be a handle having similar internal diameter characteristics as the luer while providing greater surface area for manipulating the deployment apparatus. As stated above, a preferred alternative would be a proximal handle that is similar in geometrical shape but preferably smaller than the outer handle hub, to facilitate movement, however the proximal handle may be of any size functionally acceptable by the user. The deployment apparatus is preferably sterilized by a validated sterilization cycle EtO. Moreover, the device is capable of resterilization (validated cycle) with no degradation of performance. However, it is preferable to provide a disposable device.

The deployment apparatus is preferably about 100 cm±2 cm total. The inner diameter of the inner tubular member is approximately about 1 mm and the outer diameter of the outer tubular member is preferably about 5 to 6 mm in diameter. For purposes of this discussion, the usable length of the inner tubular member shall be from the inner tubular member distal hub/handle end to the distal tip. The usable length of the outer tubular member shall be from the distal hub/handle end of the outer tubular member to the distal tip. The overall length of the device shall be from the distal hub/handle end of the outer tubular member to the distal tip of the inner tubular member when assembled and not deployed. There will also be preferably three radiopaque (platinum iridium) markers for marking the stent, the stent deployment distance, and depth. The outer tubular member is preferably manufactured of stiffer synthetic material. In a preferred embodiment, the length of the outer tubular member is preferably shorter than that of the inner tubular member.

However, these dimensions may differ as a function of the stent diameter and/or if an optical scope is employed to facilitate stent delivery. The outer tubular member may be configured to allow for the coupling of an optical scope along the outer diameter thereof. Alternatively, the inner diameter of the inner tubular member may be enlarged sufficiently to accommodate the optical scope and additionally the increased crimped stent diameter. However, it is expected, though not required, that the smallest diameter that allows for example a bronchoscope to pass will be employed in this alternative embodiment. It should be understood that through hindsight, after exposure to the present specification, one of ordinary skill would be able to adapt the current device to receive an ultra thin optical scope to the internal diameter of the device without undo experimentation and without departing from the spirit of the present objectives.

An exemplary deployment apparatus in accordance with the present invention is durable while affording adequate flexibility to navigate through anatomical lumens without kinking. To this end, it is preferable that the deployment apparatus is formed of biocompatible synthetics and in a preferred embodiment reinforced with metal structure. This should allow for deployment within an accuracy of about ±3 mm. Moreover, the stent is preferably released with a force lower than 30 Newtons at 37° C. though the force and deployment temperatures may be modified to suit the needs of specific anatomical conditions.

The inner tubular member is composed of a thin elastic synthetic material, such as polyurethane or Teflon®. At its proximal end, the inner tubular member has a standard adaptor or connector. At its distal end, the inner tubular member is equipped with a tip specific for various anatomical lumens.

The inner tubular member and the outer tubular member can be displaced relative to each other in longitudinal direction as well as in a radial direction. The deployment apparatus in accordance with the present invention can be used most advantageously for the placement of stents. Such stents are available in various embodiments of metal and/or synthetic material. They usually are composed of a fabric of metal wires, which expand by themselves as a result of their natural tension. Stents of a so-called shape memory alloy are also known. These stents have a small radial diameter at a low temperature, while they expand radially when exceeding an upper threshold temperature, so that they can keep a stenosis open in this manner. It is particularly advantageous to use stents of an alloy of nickel and titanium, the so-called nitinol.

An exemplary deployment apparatus according to the present invention can be used for the placement of various stents, whether they are self-expanding stents or stents, which require an activation. For this purpose, the stent is placed in the free space between the outer tubular member and the inner tubular member. Positioning of the stent in the deployment apparatus can be carried out in the area between the tip and the stent retaining hub at the distal end of the inner tubular member. Alternatively, in its insertion position, fasteners or other suitable retaining elements may hold the stent.

In relevant embodiments, when the stent is inserted and after the stenosis has been passed, the outer tubular member is retracted, so that the stent is released. Alternatively, the distal end of the outer tubular member may be placed about the stenosis so that the inner tubular member may be extended so that the stent is placed in direct contact with the desired location prior to expansion. A self-expanding stent then by itself assumes the expanded position. This eliminates the need for post expansion positioning techniques. With an alternative embodiment of the device, the device has fasteners that retain contact with a portion of the stent in the event that the stent needs to be retracted or repositioned. A stent suitable for such procedures would be one in accordance with the disclosure in co-pending U.S. patent application Ser. No. 10/190,770, which is incorporated herein in its entirety by this reference.

The following reference numbers and corresponding stent placement and deployment device components are used when describing the device in relation to the figures:

| | |
|---|---|
| 10 | Stent Delivery & Deployment Device |
| 12 | Guidewire |
| 14 | Proximal Handle/Female Threaded Luer |
| 16 | Hypotube |
| 18 | Safety Mechanism |
| 20 | Stop |
| 22 | Female Locking Member on the Stop |
| 24 | Tab of the Stop |
| 30 | Inner Tubular Member |
| 32 | Inner Diameter of Inner Tube |
| 40 | Handle |
| 42 | Cavity in Proximal Portion of Handle |
| 44 | Base of Handle Cavity |
| 46 | Male Locking Member |
| 48 | Inner Handle Hub |
| 49 | Outer Handle Hub |
| 50 | Outer Tubular Member |
| 52 | Outer Diameter of Outer Tubular Member |
| 54 | Distal Region of Outer Tubular Member |
| 56 | Inner Diameter of Outer Tubular Member |
| 60 | Distal Tip |
| 62 | First End of the Tip |
| 64 | Medial Region of the Tip |
| 66 | Second End of the Tip |
| 68 | Axial Passage |
| 70 | Retaining Hub |
| 72 | Distal Region of Retaining Hub |
| 74 | Proximal Hub of Retaining Hub |
| 76 | Pusher |
| 80 | Proximal Marker |
| 82 | Medial Marker |
| 84 | Distal Marker |
| 100 | Optical Scope |

Figure 2:
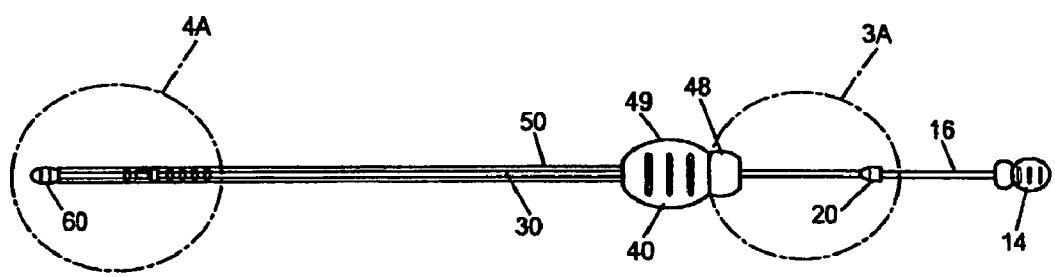
FIG. 2 is a side view of the device for delivering and deploying a radially self-expanding stent in accordance with the present invention.
Figure 3A:
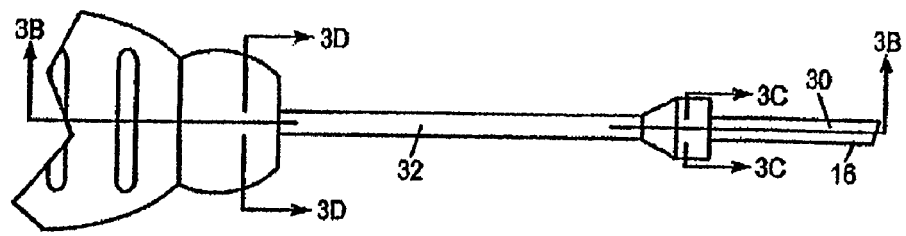
FIG. 3A depicts enlarged views of portions of the deployment safety mechanism along lines 3A-3A of the device of FIG. 2
Figure 3B:
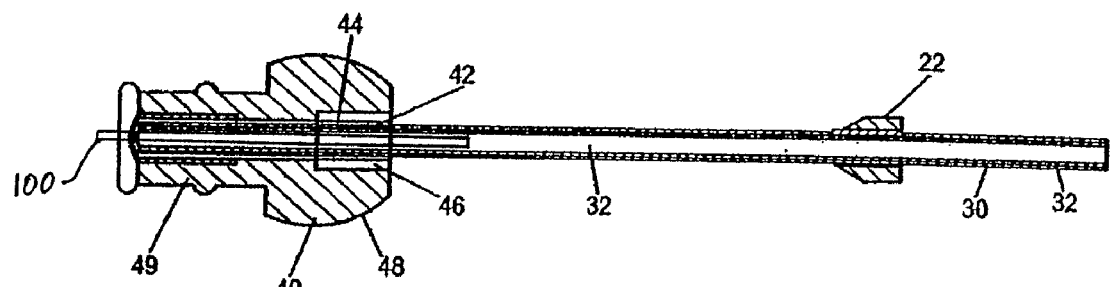
FIG. 3B shows a cross section view of the deployment safety mechanism along lines 3B-3B of FIG. 3A.
Figures 3C, 3D:
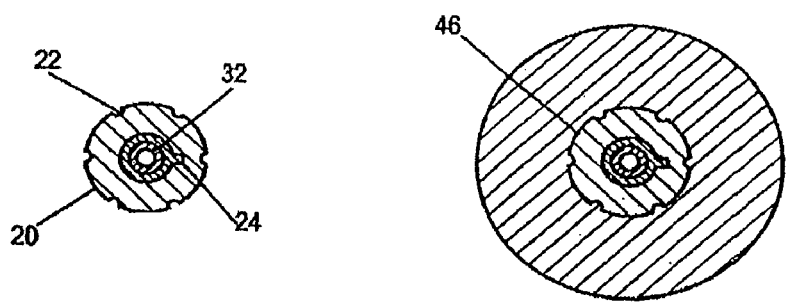
FIG. 3C is a perspective view of a portion of the complementary portion of the deployment safety mechanism region of the handle as shown along lines 3C-3C of FIG. 3A.
FIG. 3D is a perspective view of the stop of the deployment safety mechanism as shown along lines 3C-3C of the device of FIG. 3A.

The figures show an exemplary placement and deployment device 10 in accordance with the present invention. Referring in particular to FIGS. 1-2, the present invention provides a stent deployment apparatus 10 that includes an outer tubular member 50 and an inner tubular member 30, wherein the outer tubular member 50 and the inner tubular member 30 can be displaced relative to each other. At the proximal end of an exemplary device 10 is a threaded female luer 14, coupled with a portion of the inner tubular member 30 and preferably a portion of a hypotube 16. As stated earlier, a suitable alternative terminus may be employed as long as it provides the minimum benefits provided by a luer. The hypotube 16 is disposed about the inner tube 30 and extends from a location adjacent to the luer 14 through a portion of the handle 40 of the deployment apparatus 10. In an alternative embodiment, the hypotube 16 terminates within the luer 14. A safety mechanism 18 is provided that is formed in part by the complementary fitting of a portion of the handle 40 and a stop 20 coupled with the hypotube 16 between the luer 14 and the handle 40. The stop 20 is preferably molded onto the hypotube 16, the molding process resulting in a tab 24 formed on the stop 20 that is subsequently broken when the physician desires to place the deployment apparatus 10 in the proceed orientation. In an exemplary embodiment, when the tab 24 is broken and the deployment apparatus 10 is placed in the proceed orientation; the stop 20 may potentially rotate freely about the hypotube 16. It should be kept in mind that the stop 20 may take a variety of shapes, including but not limited to, rectangular, round, conical etc. In a preferred embodiment, the stop 20 is conical with a tapered effect to facilitate entrance and removal from the base handle cavity 44.

As illustrated in FIGS. 3A-3D, a preferred stop 20 includes female locking members 22 comprising channels formed along the exterior thereof that are complementary to the male locking members 46 formed on the interior cavity 42 along the proximal region of the handle 40. The cavity 42 of the handle 40 is designed to receive the stop 20 and prevent further deployment. As a result, the stop 20 is molded at a distance along the hypotube 16 such that the distance between the distal end of the stop and the base 44 of the complementary cavity 42 of the handle 40 roughly corresponds to the critical deployment point. It should be noted that the female locking members 22 and male locking members 46 of the safety mechanism 18 might be reversed so that the female locking members 22 and male locking members 46 are on the handle 40 and the stop 20, respectively. Additionally, alternative safety mechanisms may be employed to ensure accurate deployment beyond the critical deployment point.

The handle 40 is preferably molded to a portion of the outer tubular member 50, which extends from the handle 40 to the distal tip 60 of the device 10. The outer tubular member 50 is disposed about the inner tubular member 30. In an exemplary embodiment, the outer tubular member 50 is clear so that the inner tubular member 50 is visible there through. Moreover, markers 80-84 preferably formed on portions of the inner tubular member 30 are also visible through the outer tubular member 50.

Figure 4A:
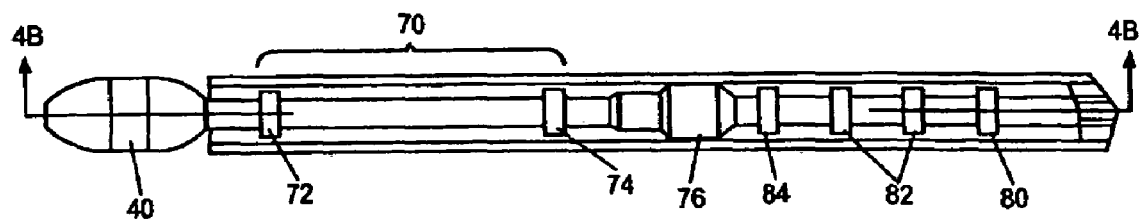
FIG. 4A is a side perspective view of the distal region of the device of FIG. 2, along lines 4A-4A.
Figure 4B:
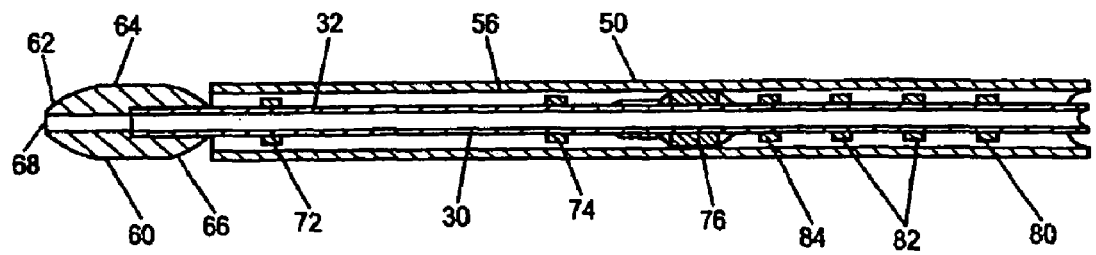
FIG. 4B depict an enlarged sectional view of the distal region of the device of FIG. 2, along lines 4B-4B.

Referring now to FIGS. 4A-4B, in the distal region 54 of the device 10, there is a stent placement hub 70, which holds the stent (not shown) during the placement procedure. In a preferred embodiment, the stent placement hub 70 comprises two double conical shaped elements, one disposed at each end of the stent and coupled with the inner tubular member 30. In an exemplary form, the distal most double conical shaped element is the distal tip of the device 60. In alternative embodiments, the stent placement hub may also comprise proximal 72 and distal 74 stops between which the stent rests in its crimped state. Moreover, the proximal end of the stent may also be restrained by conventional coupling methods (not shown) to facilitate retrieval if necessary. By way of example, which is in no way to be construed as limiting, a stent having suture disposed about its proximal end may be retained by the stent retaining hub 70 that has releasable finger-like members engaging the suture.

The device is configured such that an optional guidewire 12 may be passed through the internal diameter 32 of the device through the luer 14 at the proximal end, the distal tip 60 at the distal end and the inner tubular member 30 there between. In an alternative embodiment, the internal diameter 32 of the device 10 is sufficient to receive an optical scope (not shown) there through.

Referring to the functional aspects of the device 10, there is shown in FIG. 1 a deployment apparatus 10 that includes an elongate and flexible outer tubular member 50 constructed of at least one biocompatible thermoplastic elastomer, e.g. such as polyurethane and nylon, typically with an outside diameter 52 in the range of about between 6-9 mm. A central lumen 56 runs the length of the outer tubular member 50. A distal region 54 of the outer tubular member 50 surrounds the stent to be placed (not shown), and maintains the stent in a crimped delivery configuration, against an elastic restoring force of the stent. The stent, when in a normal unrestrained configuration, generally has a diameter (for example, 10-20 mm) substantially larger than the interior diameter 32 of the inner tubular member 30. Typically the expanded stent is larger in diameter than the body lumen in which the stent is fixed, and the restoring force tends to maintain the stent against the tissue wall.

Outer tubular member 50 is mounted at its proximal end to a handle 40. Outer tubular member 50 can be pushed and pulled relative to inner tubular 30 by hand manipulation of the handle 40 at the proximal end of the outer tubular member 50 and holding the proximal end of the handle 14.

A guidewire 12 is preferably disposed within the interior lumen 32 of an elongate and flexible inner tubular member 30, which can be constructed of materials similar to those employed to form the outer tubular member 50. However, it is preferable that inner tubular member 30 is formed from a more durable material. A distal tip 60 is coupled with inner tubular member 30 about the distal end thereof. Also attached to the inner tubular member 30 are a proximal marker 80, at least one medial marker 82 and a distal marker 84. The markers are constructed of a radiopaque material, e.g. platinum iridium, and surround the inner tubular member 30. Markers 80, 82 and 84 are axially spaced apart to mark the length of the stent and to mark the critical deployment distance for that stent length. The markers identify a stent-retaining hub 70 of the inner tubular member 30, more particularly the distal region of the inner tubular member 30 is surrounded by stent 12. The markers may also be of varying sizes and shapes to distinguish distance between distal and proximal regions. Markers 80 and 84 may have outer diameters slightly smaller than the interior diameter of outer tubular member 50. The outer tubular member 50 thus functions as a carrier for the stent, with inner tubular member 30 providing a retaining means for radially compressing the stent and maintaining the stent along the stent retaining hub 50, so long as the outer tubular member 50 surrounds the stent.

In an alternative embodiment, items 72 and 74 are marker bands (not retaining hubs) formed on the outer tubular member 50. These marker bands visually mark the ends of the stent and thus will be over the step area of the tip and the pusher 76. All the marker bands—including 80, 82 and 84 are preferably either Platinum Iridium or Stainless Steel. Moreover, the marker bands of 80, 82, and 84 will be depth marks and will be spaced in preferably 1 cm intervals. These depth marks are preferably formed on the inner tubular member 30 and are a visual aid for the physician to assist with determining the depth at which the stent has been advanced.

Inner tubular member 30, along its entire length, has an interior lumen 56 open to both the proximal and distal ends of the inner tubular member 30. An axial passage 68 through distal tip 60 continues lumen 32 to allow the guidewire 12 to pass from the luer 14 through the distal tip 60.

Handle 40 and outer tubular member 50 are movable relative to inner tubular member 30. More particularly, the handle 40 is moved proximally relative to the stent-retaining hub 70, facilitating the movement of outer tubular member 50 relative to inner tubular member 30 so as to provide a means for controllably withdrawing the outer tubular member 50, relative to the inner tubular member 30, resulting in the release of the stent for radial self-expansion.

When the device 10 is used to position the stent, the initial step is to position guidewire 12 within the anatomy of a patient. This can be accomplished with a guide cannula (not illustrated), leaving guidewire 12 in place, with the exchange portion of the guidewire extended proximally beyond the point of entry into the anatomy of the patient. Deployment apparatus 10 is then advanced over the guidewire 12 at the exchange portion, with the guidewire 12 being received into passage 68 of distal tip 60. As device 10 is inserted into the body, the proximal portion of guidewire 12 travels proximally (relative to the device) to the proximal end of guidewire lumen 32.

Once device 10 is positioned, the physician maintains a guidewire 12 and inner tubular member 30 substantially fixed with one hand, while moving handle 40 in the proximal direction with the other hand, thus to move outer tubular member 50 proximally relative to inner tubular member 30. As the outer tubular member 50 is retracted, the stent remains substantially fixed relative to inner tubular member 30, and thus radially self-expands. As the handle 40 and correspondingly the outer tubular member 50 is retracted, the handle 40 encounters the safety mechanism 18 for the critical deployment point. The inner tubular member 30, via the handle 14, may have to be rotated to align and insert the stop 20 into the handle 40. When fully inserted, further deployment cannot occur without twisting and snapping the tab 24 portion of the stop 20. Continued retraction of the outer tubular member 50 results in complete deployment of the stent.

After deployment, the stent ideally radially self-expands to a diameter greater than the diameter of outer tubular member 50. Accordingly, device 10 can be withdrawn proximally through the stent. However, in the event that the stent does not radially expand fully, distal tip 60 is configured to facilitate removal of deployment apparatus 10 through the lumen of the stent.

Guidewire 12 can be withdrawn as well. The guidewire 12 emerges from the proximal end of the luer 14. However, should the medical procedure involve further treatment, e.g., placement of a further stent, the deployment apparatus 10 can be removed without removing the guidewire 12. Device 10 is removed by progressively pulling the device away from the guidewire 12 (which removes the guidewire from within the inner tubular member 30), all while maintaining guidewire 12 in place.

Figure 6:
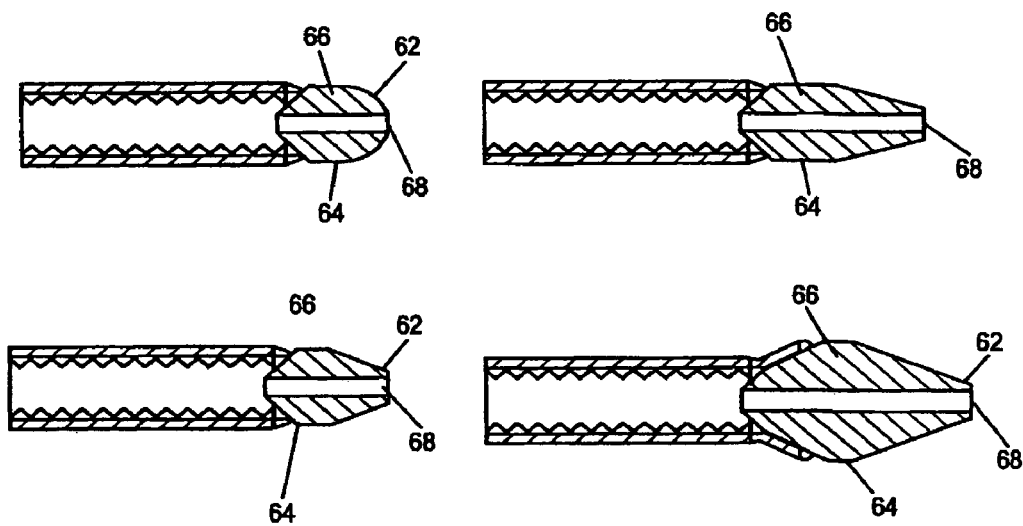
FIG. 6 illustrates cross-sectional views of various configurations of a distal tip according to additional embodiments of the present invention.

Returning to distal tip 60, as illustrated in FIGS. 4A-4B and 6, distal tip 60 can have a variety of confirmations, but by way of non-limiting example, distal tip 60 comprises first 62 and second 66 ends having a smaller diameter than the medial region 64 thereof. In a preferred embodiment, each end is conical in shape so as to allow the tip 60 to wedge through an incompletely expanded stent when pulled proximally with respect to the stent. Moreover, the dual conical end design facilitates removal but sufficiently prevents the crimped stent from releasing from the stent retaining hub 70 and prematurely expanding. Distal tip 60 may alternatively have a flared medial region 64 so as to facilitate retrieval and retraction of a misaligned stent 12.

With respect to additional safety features incorporated in the present device 10, in a preferred embodiment, the device 10 has a deployment safety mechanism 18 that comprises male 46 and female 22 locking members that are brought into functional engagement as the stent is being deployed. Once the stent has reached the critical deployment point, the distal end of the stop 20 is substantially flush with the base 44 of the handle cavity 42 and the female locking members 22 of the stop 20 are in operative communication with the corresponding male locking members 46 formed on the interior surface of the cavity 42 of the handle. When the safety mechanism 18 is engaged as described above, the stent cannot be deployed further without physician intervention. In order to deploy the stent beyond this point, the physician has to rotate the stop 20 to cause the tab 24 to break. Once the tab 24 is broken, the device 10 is in the proceed orientation and deployment may proceed.

In a preferred embodiment, the physician will feel a tactile indication that the device 10 can be deployed further. Alternatively, the breaking of the tab may also, or as a substitute to tactile indication, results in an audible indication that further deployment is possible. Additionally, the physician is apprised of the fact that deployment beyond this point is irreversible except for interventional retrieval methods. As discussed earlier, the critical deployment point is preferably about 60% deployment, beyond which retraction is not recommended. As a result, the safety mechanism 18 removes the need to estimate extent of deployment and provides a reliable means of accurately deploying stents. Alternative locking mechanisms may be provided as long as they retain the important characteristic of giving the physician a sensory indication of extent of stent deployment and removes the need to estimate extent of deployment. By way of non-limiting example only, the locking mechanism could comprise a breakable seal, tab/stop lock, diverted channel locking mechanism, etc.

Figure 5:
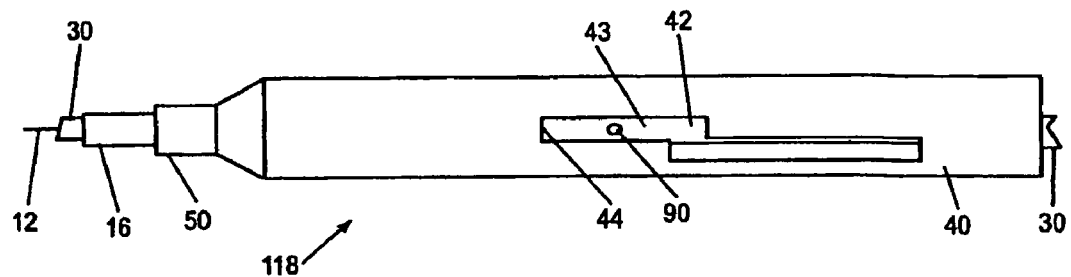
FIG. 5 illustrates a safety mechanism according to one embodiment of the present invention.

Referring particularly to FIG. 5, an alternative safety mechanism 118 is presented that is a principally a diverted channel mechanism. In practice, a detent 90 formed preferably on the hypotube has free proximal/distal travel to the critical deployment point at which time physician intervention is required to continue deployment. In a preferred embodiment, the Inner Tubular Member 30 is rotated until the travel of the detent is no longer obstructed. The channel in which the detent travels may be of a variety of geometrical shapes such as M, W, L, S Z, etc: the preferred geometry being substantially Z shaped, as shown in FIG. 5.

In an additional embodiment (not shown) of deployment safety mechanism 118, the device 10 has a deployment safety mechanism that comprises male and female locking members that are brought into functional engagement as the stent 12 is being deployed. Once the stent 12 has reached the critical deployment point, the male locking member cannot be advanced further because of a detent formed on the inner diameter of the outer tubular member catches the cavity formed on the corresponding portion of the male locking member. As a result, in order to further advance the device 10 to fully deploy stent 12, the inner tubular member must be rotated so as to break the detent. Once the detent is broken, the physician will feel a tactile indication that the device 10 can be deployed further.

Alternatively, the breaking of the detent may also, or as a substitute to tactile indication, results in an audible indication that further deployment is possible. Additionally, the physician is apprised of the fact that deployment beyond this point is irreversible except for interventional retrieval methods. As discussed earlier, the critical deployment point is preferably about 60% deployment, beyond which retraction is not recommended. As a result, the safety locking system 60 removes the need to estimate extent of deployment and provides a reliable means of accurately deploying stents. Alternative locking mechanisms may be provided as long as they retain the important characteristic of giving the physician a sensory indication of extent of stent deployment.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A device for allowing a user to deploy a stent in an anatomical lumen of a patient, the device comprising:

a longitudinally extending inner tubular member having distal and proximal ends, the distal end comprising a tip;

a longitudinally extending outer tubular member having an outer and inner diameter, the outer tubular member being longitudinally and axially displaceable relative to the inner tubular member;

a handle, coupled with a portion of the outer tubular member, the handle having first and second ends and the second end defining a cavity having at least one stop compatible male or female locking member formed therein;

a stop formed about the inner tubular member, the outer surface of the stop comprising at least one female or male locking member configured to coaxially engage the male or female locking member, respectively, of the handle cavity to form a safety mechanism, wherein the locking members are configured to engage one another along an axis coaxial to a longitudinal axis of the inner and outer tubular members;

wherein the outer tubular member and inner tubular member are axially displaceable relative to each other without requiring rotational motion with respect to one another to a predetermined threshold corresponding to partial deployment of a stent and engagement of the locking members absent intervention by the user of the device such that relative axial displacement of the outer tubular member and inner tubular member and a corresponding degree of stent deployment is limited by the safety mechanism absent the user intervention.

2. The device of claim 1, wherein the inner tubular member defines a lumen longitudinally extending substantially the distance from the distal end to the proximal end of the inner tubular member, which allows a guidewire to extend through the lumen thereof.

3. The device of claim 1, wherein the user intervention comprises displacing the outer tubular member axially relative to the inner tubular member.

4. The device of claim 3, wherein an audible indication follows the user intervention.

5. The device of claim 3, wherein a tactile indication follows the user intervention.

6. The device of claim 3, further comprising at least one tab formed on the stop, which serves as the audible indication when broken during user intervention.

7. The device of claim 3, wherein the outer tubular member when moved longitudinally relative to the inner tubular member in a proximal direction away from the selected location, releases the stent for radial self-expansion.

8. The device of claim 1, wherein the predetermined threshold is about between 10% and 90% deployment.

9. The device of claim 8, wherein the predetermined threshold is about 60% deployment.

10. The device of claim 1, wherein a guidewire is coupled to a portion of the outer diameter of the outer tubular member.

11. The device of claim 1, wherein the inner tubular member is configured to receive an optical scope.

12. The device of claim 1, wherein the outer tubular member is clear.

13. The device of claim 12, wherein the outer tubular member is kink resistant.

14. The device of claim 1, wherein there is at least one marker coupled with a portion of the inner tubular member.

15. The device of claim 1, wherein the inner tubular member is of a material that is kink resistant.

16. The device of claim 1, wherein the distal end comprising the tip has first, medial and second sections, the first and second sections having outer diameters that are less than that of the medial section.

17. The device of claim 1, wherein a portion of the inner tubular member about the proximal end further comprises a stent carrier adapted to carry a radially self-expanding stent in a radially contracted state.

18. The device of claim 17, further including a radially self expanding stent carried by the stent carrier, extended along and surrounding at least part of the distal end region, and surrounded by a portion of the outer tubular member and thereby maintained in the radially contracted state.

19. The device of claim 1, wherein the cavity of the handle has at least one stop compatible male or female locking member integrally formed therein.

20. The device of claim 1, further comprising a hypotube having a first end, a second end, an outer surface, an inner surface, wherein the stop is formed on the hypotube between the first and second ends.

21. The device of claim 1, wherein the cavity is defined circumferentially about the outer tubular member.

22. The device of claim 1, wherein the stop is disposed circumferentially about the inner tubular member.

23. The device of claim 1, wherein the handle has proximal and distal ends, and wherein the cavity is defined in the proximal end of the handle.

24. The device of claim 23, wherein the stop is positioned proximally of the cavity such that the stop is configured to engage the cavity when the handle is displaced in a proximal direction.

25. The device of claim 1, wherein the stop is spaced distally from the proximal end of the inner tubular member.

26. The device of claim 1, wherein the outer tubular member is configured to partially overlie the stent at the predetermined threshold.

27. A device for allowing a user to deploy a stent in an anatomical lumen of a patient, the device comprising:

a longitudinally extending inner tubular member having distal and proximal ends, the distal end comprising a tip;

a longitudinally extending outer tubular member having an outer and inner diameter, the outer tubular member being longitudinally and axially displaceable relative to the inner tubular member;

a handle, coupled with a portion of the outer tubular member, the handle having first and second ends and the second end defining a cavity having at least one stop compatible male or female locking member formed therein, wherein the cavity is disposed around a circumference of the outer tubular member;

a stop disposed about the inner tubular member, the outer surface of the stop comprising at least one female or male locking member configured to coaxially engage the male or female locking member, respectively, of the handle cavity to form a safety mechanism;

wherein the outer tubular member and inner tubular member are axially displaceable relative to each other without requiring rotational motion with respect to one another to a predetermined threshold corresponding to partial deployment of a stent and engagement of the locking members absent intervention by the user of the device such that relative axial displacement of the outer tubular member and inner tubular member and a corresponding degree of stent deployment is limited by the safety mechanism absent the user intervention.

28. A device for allowing a user to deploy a stent in an anatomical lumen of a patient, the device comprising:

a longitudinally extending inner tubular member having distal and proximal ends, the distal end comprising a tip;

a longitudinally extending outer tubular member having an outer and inner diameter, the outer tubular member being longitudinally and axially displaceable relative to the inner tubular member;

a handle, coupled with a portion of the outer tubular member, the handle having first and second ends and the second end defining a cavity having at least one stop compatible male or female locking member formed therein;

a stop disposed around a circumference of the inner tubular member, the outer surface of the stop comprising at least one female or male locking member configured to coaxially engage the male or female locking member, respectively, of the handle cavity to form a safety mechanism;

wherein the outer tubular member and inner tubular member are axially displaceable relative to each other without requiring rotational motion with respect to one another to a predetermined threshold corresponding to partial deployment of a stent and engagement of the locking members absent intervention by the user of the device such that relative axial displacement of the outer tubular member and inner tubular member and a corresponding degree of stent deployment is limited by the safety mechanism absent the user intervention.

* * * * *